US005919489A

United States Patent [19]

Saleki-Gerhardt et al.

[11] Patent Number: 5,919,489

[45] Date of Patent: Jul. 6, 1999

[54] PROCESS FOR AQUEOUS GRANULATION OF CLARITHROMYCIN

[75] Inventors: Azita Saleki-Gerhardt, Libertyville; Ernest Richard Keske, Waukegan, both of Ill.

[73] Assignee: Abbott Laboratories, Abbott Park, Ill.

[21] Appl. No.: 08/722,288

[22] Filed: Oct. 9, 1996

Related U.S. Application Data

[60] Provisional application No. 60/007,150, Nov. 1, 1995.

[51] Int. Cl.[6] .............................. A61K 9/16; A61K 47/32

[52] U.S. Cl. .......................... 424/501; 514/952; 514/974; 514/772.6

[58] Field of Search .................................... 424/497, 501; 514/974, 952, 722.6; 428/402

[56] References Cited

U.S. PATENT DOCUMENTS 4,608,278 8/1986 Frank et al. ............................ 424/497
4,808,411 2/1989 Fu Lu et al. .

OTHER PUBLICATIONS

Fu Lu, M. F., et al., "A Polymer Carrier System For Taste Making Of Macrolide Antibiotics", Research Article, pp. 706–712.

*Primary Examiner*—Edward J. Webman
*Attorney, Agent, or Firm*—Mona Anand

[57] ABSTRACT

The present invention provides a process for the aqueous granulation of a macrolide antibiotic which comprises mixing a macrolide antibiotic and a carbomer; wetting the mixture with water; and blending the mixture to allow formation of a macrolide antibiotic-carbomer granule.

18 Claims, 8 Drawing Sheets

PROCESS FOR AQUEOUS GRANULATION OF CLARITHROMYCIN

CROSS REFERENCE TO RELATED APPLICATIONS

This application claims benefit of U.S. Provisional Application No. 60/007,150, filed Nov. 1, 1995.

TECHNICAL FIELD

This invention relates to a process for preparing pharmaceutical granules of macrolide antibiotics, such as granules consisting of clarithromycin and acrylic acid carbomers. More particularly, the invention relates to an improved process for the preparation of such granules wherein no organic solvents are utilized.

BACKGROUND OF THE INVENTION

Macrolide antibiotics have been used extensively in treating a wide range of bacterial infections. The macrolide antibiotic, 6-O-methylerythromycin A (clarithromycin), is particularly useful in treating common pediatric infections of the middle ear and upper respiratory tract. When macrolide antibiotics are administered to children and other patients who experience difficulty or reluctance in swallowing solid dosage forms (such as tablets or capsules), liquid formulations such as solutions, emulsions, and suspensions are preferred. However, macrolide antibiotic are extremely bitter, and even trace quantities dissolved in liquid dosage form are often perceived as unpalatable. Consequently, it has been sought to mask the taste of such drugs by preparing them as suspensions, in a flavored liquid, of fine particles which are coated or sealed with an agent that prevents the dissolution of the drug until after the particles have been swallowed. In this manner, adequate taste masking has been achieved while maintaining the desired pharmacokinetic properties. The most favorable results to date have been obtained with oral liquid suspensions in which the above particles consist of complexes or absorbates of a macrolide antibiotic and a carbomer, as described in U.S. Pat. No. 4,808,411, issued to Fu Lu et al. on Feb. 28, 1989.

These complexes or absorbates are typically prepared by dissolving the drug in a mixture of acetone and alcohol and adding carbomer, or by mixing a slurry of the drug and carbomer in acetone or an acetone/alcohol mixture. However, utilization of the aforementioned processes on an industrial scale presents a number of problems, including employee safety, emissions of solvent vapors to the atmosphere, and cost. Accordingly, a particular need exists for a process which does not employ alcohol or organic solvents.

SUMMARY OF THE INVENTION

In a first aspect, the invention provides a process for preparing granules of a macrolide antibiotic, comprising the steps of:

(a) mixing a macrolide antibiotic and a carbomer in a weight ratio of between about 1:10 and about 5:2;

(b) wetting the mixture with an aqueous solvent;

(c) blending the mixture for a time sufficient to allow formation of macrolide antibiotic-carbomer granules, said blending being accomplished in a vessel having a head space which is maintained at a temperature from about 0 to about 70° C.; and (d) drying the macrolide antibiotic-carbomer granules.

Preferably, the carbomer is an acrylic polymer such as CARBOPOL 974P acrylic acid polymer and the antibiotic macrolide is selected from the group consisting of an erythromycin and a clarithromycin, preferably clarithromycin. Generally the mixture formed in step (a) comprises clarithromycin and acrylic polymer in a ratio of between about 1:10 and about 5:2, usually about 5:3 and the mixture is wetted in step (b) with between about 1.5 and about 2.5 parts water by weight. Optimally, the aqueous solvent of step (b) is essentially free of organic solvents.

In a variation, the process described above further comprises the additional step, prior to step (d), of mixing the macrolide antibiotic-carbomer granules formed in step (c) with an aqueous solution of a binder, typically polyvinylpyrrolidone.

Optimally, the reaction temperature is maintained between about 30 to about 50° C., ideally around 40° C. The temperature may be maintained by means of a water jacket, typically at about 20 to about 40° C.

In another aspect, the invention provides pharmaceutical granules comprising clarithromycin and a carbomer prepared according to any of the processes described above.

In another aspect, the invention provides a method for increasing the hardness of pharmaceutical granules of macrolide antibiotic-carbomer, comprising the steps of (a) mixing the granules with an aqueous solution of a binder, typically polyvinylpyrrolidone; and (b) drying the granules.

The clarithromycin-carbomer granules formed in this process are comparable to those formed using alcohol or alcohol/acetone mixtures in terms of taste masking and suitability for use in liquid dosage forms.

BRIEF DESCRIPTION OF THE DRAWING FIGURES

DETAILED DESCRIPTION

Figure 1:
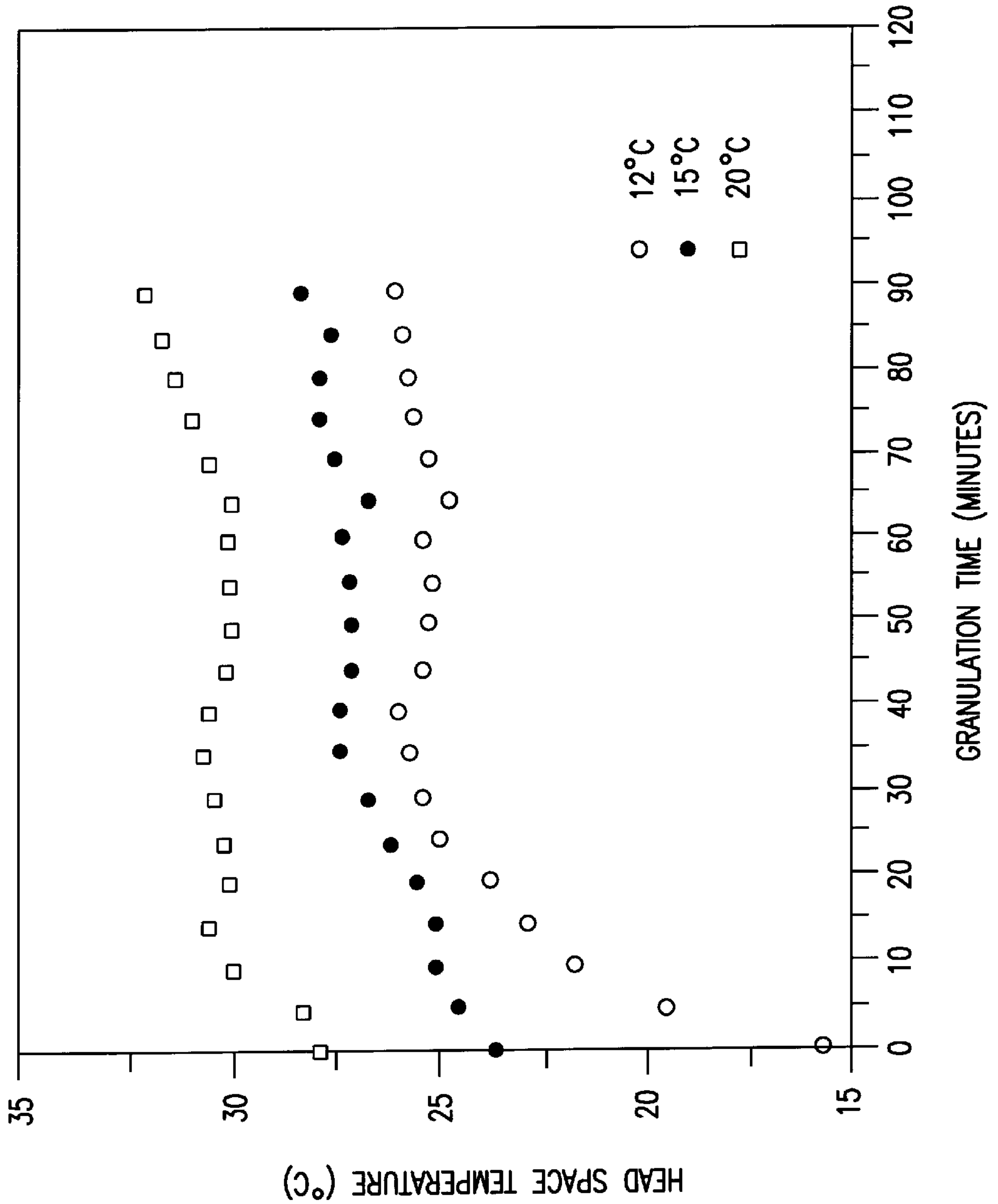
FIG. 1 shows a graph of head space temperature as a function of granulation and jacket temperature for clarithromycin-CARBOPOL 974P granulations in a 600 liter GRAL.

The term "macrolide antibiotic" as used herein, refers to a compound typically characterized by having a 14-membered macrolactone ring and two O-linked sugar molecules, such as are found in erythromycins A, B, C and D. Useful macrolide antibiotics include but are not limited to erythromycin, dirithromycin, josamycin, midecamycin, kitasamycin, tylosin, roxithromycin, rokitamycin, oleandomycin, miocamycin, flurithromycin, rosaramicin, azithromycin and clarithromycin.

Clarithromycin compounds (6-O-methylerythromycins) are a subset of macrolide antibiotics represented by the formula:

(I)

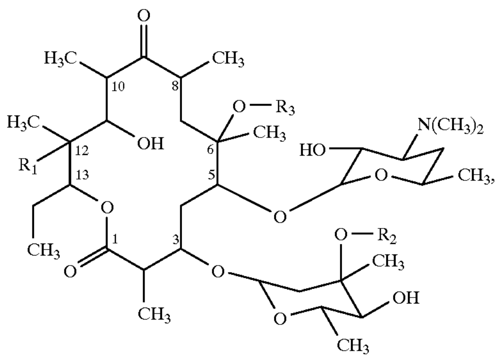

wherein $R_1$ is either OH or H, $R_2$ is either $CH_3$ or H and $R_3$ is $CH_3$. There are several types of clarithromycins. For example, clarithromycin A is a compound of formula I wherein $R_1$ is OH, $R_2$ is $CH_3$, and $R_3$ is $CH_3$. Clarithromycin B is a compound of formula I wherein $R_1$ is H, $R_2$ is $CH_3$, and $R_3$ is $CH_3$. Clarithromycin C is a compound of formula I wherein $R_1$ is OH, $R_2$ is H, and $R_3$ is $CH_3$. Clarithromycin D is a compound of formula I wherein $R_1$ is OH, $R_2$ is H, and $R_3$ is $CH_3$. Although no particular form of clarithromycin or macrolide antibiotic is essential for the operation of the present invention, clarithromycin A is presently preferred.

A process of the present invention involves forming a granulated product (i.e., "granules") of a macrolide antibiotic (such as clarithromycin) and a carbomer, in the presence of water alone. As used herein, the term "granule(s)" refers to a composition of matter comprising from about 25% to about 90% of a macrolide antibiotic and from about 10% to about 75% of a carbomer." While not intending to be limited by any particular theory, the granule is believed to be held together by interactions such as (i) the ionic attraction between the amino sugar group of typical macrolide antibiotics and the carbonyl group of the carbomer, and (ii) the gel properties of the carbomer.

The carbomers employed in this invention are branched acrylic acid polymers with a high degree of cross linking and thickening capacity. They have the general formula:

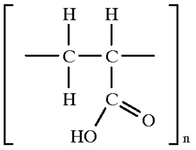

where n is from about 10,000 to about 60,000. The average equivalent weight is 76, while the molecular weight is approximately 3 million. In its presolvated state, the carbomer is a tightly coiled molecule and its thickening properties are limited. However, due to its relatively high molecular weight and extensive resin cross linking, the carbomer can generate a high viscosity gel. This gelation is initially believed to occur as a result of hydration and partial uncoiling. Neutralization of the acidic groups of the carbomer with a suitable base organic or inorganic base is required to further uncoil the molecule and generate high viscosity solutions.

Traditionally the formation of a macrolide antibiotic/carbomer granule was achieved by first producing a medicinal salt of the desired carbomer by dispersing it in a solvent and then neutralizing the resulting polymer with various amines or inorganic bases (Secard, 1962; Bremecker, 1989; Misek et al., 1956). Alternatively, when carbomer salt formation could not be achieved, a drug was physically entrapped in a solid carbomer matrix gel. In this technique, after dispersion of the drug in a carbomer, the gel structure collapsed, leading to entrapment of the drug molecules in the carbomer matrix (Secard, 1962). In both aforementioned techniques, the drug was added only after the polymer was completely dispersed in the appropriate solvent.

The preparation of certain macrolide antibiotic/carbomer granules, in particular, uncoated clarithromycin granules, is somewhat unique as the interaction of drug and a carbomer can take place in the solid state and both clarithromycin and carbomer are present when the granulating solvent is added. The solvent is added over a time period sufficient for effective interaction between clarithromycin and the carbomer molecules. Since the interaction between clarithromycin and carbomer is expected to occur in the solid state, the physical properties of a particular carbomer as a dry solid should also be considered, as these properties play a significant role in its interaction with clarithromycin.

An example of a suitable carbomer is CARBOPOL 974P. In addition to having the above mentioned properties, CARBOPOL 974P is recommended for use in the pharmaceutical industry due to its high purity grade and extensive toxicity studies. This particular carbomer can generate a high viscosity gel due to its relatively high molecular weight (i.e., average MW of approximately 3,000,000) and extensive resin cross linking. Initially, gelation of this polymer is believed to occur as a result of partial swelling by water molecules. However, neutralization of the acidic groups of this polymer with an organic or inorganic base leads to further enhancement of viscosity and gelation.

"Granulation" normally refer to the process of bringing fine powders into larger and larger particle size by binding them together. In the present application, "granulation" is used in a similar manner to describe the bringing together of the macrolide drug and the carbomer polymer into larger and larger complexes.

In the initial process of forming macrolide antibiotic "granules", a macrolide antibiotic such as clarithromycin A and a suitable carbomer are added together, in dry form, in a suitable mixing vessel. A mixing vessel is any device which mixes or blends the desired macrolide antibiotic and carbomer. Preferably, the mixing device includes a granulator. A granulator is a particular device which blends or mixes one or more chemical compounds in granular form, typically having a defined size range. Preferably, a mixing vessel is also equipped with a means of measuring head space temperature. "Head space" as used herein, refers to the air space existing between the compound or compounds contained in the granulator and the internal side of the granulator lid. "Head space temperature" refers to the temperature of the air in the head space and is indicative of the temperature of the mixture contained within the vessel. An example of means for measuring head space temperature is a temperature probe which may be inserted through the lid of the granulator into the head space region. Granulators of the type described are well known to those of ordinary skill in the art.

The type of mixing vessel chosen depends on the volume of drug and carbomer the user intends to mix. For example, on a small scale, the drug and carbomer may be mixed in stainless steel bowls or mortars. On a larger scale, twin shell blenders such as the Patterson-Kelley twin-shell blender, or planetary mixers such as the Glen mixer and the Hobart mixer may be used. A preferred mixing device utilizes a high sheer granulator such as the GRAL system (Colette Manufacturing Co.).

According to the inventive process, 6-O-methylerythromycin A and carbomer in a ratio of between 1:10 and 5:2, preferably in a ratio of 5:2 to 5:3, are mixed or blended together dry. The carbomer may be any acrylic acid polymer capable of gelation at suitable temperature and concentration in water. A preferred carbomer is CARBOPOL 974P, NF (commercially available from B. F. Goodrich Co.).

In the next step of the process, the mixture is wetted with water, preferably in the absence of an organic solvent and mixed for an amount of time sufficient for granulation to occur. As used herein, the term "organic solvent" refers to any organic compound capable of dissolving either the macrolide antibiotic of interest or the carbomer of interest. Representative examples include alcohols, such as ethanol or isopropanol, ethers and acetone. The term "essentially in the absence of" means that the aqueous solvent either completely lacks any organic solvent or contains only trace amounts of an organic solvent as an impurity. "Essentially in the absence of" is meant to encompass the notion that the presence of organic solvents during the granulation of a macrolide antibiotic and carbomer is neither intended or desirable.

In general, increasing the amount of water to the drug-carbomer mixture increases the efficiency of the drug-carbomer interaction. This more efficient interaction may be attributed to the role of water in enhancing the flexibility of the carbomer and to the increased concentration of drug in the aqueous phase. However, increasing water concentration eventually leads to formation of a paste which is difficult to dry. Thus, in the most preferred embodiment, 1.5 to 2.5 kg of water to 1 kg of powder is added over 60 minutes, followed by mixing for an additional 30 to 60 minutes.

The formation of drug-carbomer granules is accompanied by the generation of heat due to the drug-carbomer interaction. It is desirable, however, to maintain the temperature of the reaction between about 20 and 70° C. The reaction temperature may be controlled by any suitable means, for example, by a water jacket around the reaction vessel. The reaction temperature may be monitored by any suitable thermosensor means, e.g., by a temperature probe inserted into the head space or reaction mixture. In general, the quality of the granules obtained increases with increasing temperature, up to about 70° C., above which the macrolide antibiotic tends to degrade. At the same time, the granulation process is retarded by overcooling. Thus, the optimal temperature is dependent on several factors, but generally involves tradeoffs between better granulation and ease of processing.

A preferred means for maintaining the reaction temperature is by means of a water jacket surrounding the vessel. Thus, a convenient means of monitoring the temperature is by monitoring the inlet and outlet temperatures of the water jacket. Of course, this is done after taking into account the size of the mixing vessel, the volume of head space and the typical head transfer losses from the reaction mixture to the water jacket. For example, in a 600 L GRAL, high sheer granulator having a batch size of about 60–120 kg material, a preferred temperature for the head space is about 30–35° C., which translates to a cooling jacket temperature from about 20° C.–25° C.

The granules are then dried, for example, in a drying oven or a fluid-bed dryer and sized, using, for example a Sweco system. Such drying systems are well known to those of ordinary skill in the art. For use in pediatric suspensions, granules having a particle size between 40 and 80 mesh (420–177 microns) are desired. Granules which do not pass through the 40 mesh screen may be milled to increase the yield of 40–80 mesh particles. Hammer mills such as the FitzMill Comminutor or fluid-air mills are most effective in reducing particle size.

For more effective taste masking, and increased ability to remain intact during further processing, harder granules are desired. The hardness of the granules may be increased by a second granulation using a binder, which serves to impart additional cohesiveness to the granule. Suitable binders include starch, gelatin, and sugars such as sucrose, glucose, dextrose, molasses, and lactose, and natural and synthetic gums such as acacia, sodium alginate, extract of Irish moss, panwar gum, ghatti gum, mucilage of isapol husks, carboxymethylcellulose, methylcellulose, poylvinylpyrrolidone, Veegum, and larch arabogalactan. Other possible binders include polyethylene glycol, ethylcellulose, waxes, water, and alcohol. While water and alcohol are not true binders, their solvent action on the drug-carbomer granule may assist the conversion of the powdered material to granules. A preferred class of binders is the polyvinylpyrrolidinones (PVP's). A particularly preferred binder is POVIDONE (PVP K-90) available from ISP Technology Inc. (Wayne, N.J.). The binder may be dispersed in dry form followed by wetting with the appropriate solvent, added to a slurry or suspension of the drug-carbomer granules in the appropriate solvent, or used in a granulating solution. In a preferred embodiment, the particles obtained after drying the initial granulation are granulated a second time using a solution of PVP K-90 in distilled water or ethanol, followed by sizing and milling as described above. In the most preferred embodiment, a 10–15% solution of PVP K-90 in distilled water is used for the second granulation. An unexpected result of aqueous granulation is the increased hardness of the granules relative to the granules produced by the prior art methods where alcohol is used instead of water as the granulating solvent.

The relative hardness of granules produced in aqueous and alcohol granulation is shown in Table 1. Relative hardness was determined using the sieve hardness test described by Krycer and Pope in "An Evaluation of Tablet Binding Agents, Part I: Solution Binders", *Powder*

*Technology,* 1983, 34, 39–51. In this technique, a nest of screens (40 and 80 mesh and pan), a sieve shaker (Model No. SS-15, Gilson Sieve Co.) and 12 ceramic balls, each weighing about 16 grams and of similar size were utilized. The ceramic balls were placed on the 80 mesh screen and the 40–80 mesh granules were placed on top of the 40 mesh screen and shaken for different time intervals. The mass of particles passing through the 80 mesh screen provides useful information about the relative hardness of the granules.

TABLE 1

Relative hardness of granules produced in alcohol and aqueous granulation

| Sieve Time | % Fines After Initial Granulation | % Fines After PVP Granulation | % Fines After Alcohol Granulation |
|---|---|---|---|
| 10 | 8.1 | 4.1 | 10 |
| 20 | 12.4 | 7.4 | 14 |
| 30 | 18.3 | 11 | 16 |

The sizing and milling process described above generates up to 30% fines (particles which pass through an 80 mesh screen). The yield of desired 40–80 mesh particles can be increased by regranulating the fines with distilled water, or a 2–3% solution of PVP in distilled water. The yield of 40–80 mesh particles obtained in this regranulation step is typically about 50%.

The taste protection afforded by the aqueous granulation of 6-O-methylerythromycin A is further enhanced by polymer coating of the granules. A variety of polymeric materials can be employed, including, but not limited to ethyl cellulose, hydroxypropyl cellulose, hydroxypropylmethyl cellulose, polyvinyl acetate phthalate, cellulose acetate phthalate, hydroxypropylmethyl cellulose phthalate, and shellac. Other polymers commonly known by trade names include EUDRAGIT E-100, S-100, AND L-100, available from Rohm and Haas Company. The most preferred coating is hydroxypropylmethyl cellulose phthalate.

The foregoing may be better understood by the following Examples, which are presented for purposes of illustration and are not intended to limit the scope of the invention.

GENERAL EXPERIMENTAL PROCEDURES

1. General Preparation of Uncoated Clarithromycin Particles a. First Granulation During the first granulation, clarithromycin particles were initially mixed with CARBOPOL 974P in a 5:3 mass ratio for 15 minutes to assure good mixing. The mixture was then granulated with distilled water for different time periods and at different temperatures. After granulation was completed, the granules were transferred to a fluid bed dryer and dried for at least one hour, or until a loss on drying (LOD) value of less than 5% was achieved.

b. Second Granulation

In the second granulation, the dried clarithromycin-CARBOPOL 974P granules were regranulated with a solution of polyvinylpyrrolidone (PVP) in distilled water. At the end of this granulation step, the material was once again dried in a fluid bed dryer until reaching a LOD value (see below) of less than 2%.

c. Regranulation

The fine particles (i.e., fraction of material passing through an 80 mesh screen) produced as a result of milling and processing were regranulated in order to increase the particle size and improve the overall yield of 40–80 mesh uncoated Clarithromycin particles. In the regranulation process, distilled water was utilized as the granulating solvent (unless otherwise specified) in order to maintain the concentration of PVP constant throughout the formulation.

2. In-Process Temperature Control Measurements

A thermocouple (52 K/J type thermometer, John Fluke Manufacturing, Everett, Wash.) was inserted in the head space above the granulating solid and measurements were recorded periodically for all the experiments performed in 75, 600 and 1200 liter GRALs.

The jacket temperature in the 10 liter GRAL was controlled using a circulating water bath. Due to the limited capacity of circulating water available, the jacket temperature for the 75 liter GRAL was controlled using cold tap water, where both inlet and outlet jacket temperatures were recorded at five minute intervals. The jacket temperature of the 600 liter GRAL was controlled using an in-house cooling system. Mixer and chopper power readings for all experiments in the 75, 600 and 1200 liter GRALs were monitored and recorded as a function of time.

3. Granule Hardness Test

The relative hardness of granules produced after each granulation step was examined using a sieve hardness test (Krycer and Pope, 1983). Since the desired particle size range for uncoated Clarithromycin particles is between 40–80 mesh, measurement of the fraction of material passing through an 80 mesh screen provides useful information regarding the relative hardness of these particles. In this technique, a nest of screens (40, 80 mesh and pan), a sieve shaker (Model No. SS-15, Gilson Sieve Co.), and 12 ceramic balls (with each ball weighing approximately 16 grams and all balls of a relatively similar size), placed on the 80 mesh screen were utilized. The 40–80 mesh uncoated Clarithromycin particles were placed on top of the 40 mesh screen and then shaken for different time intervals. The mass of granules passing through the 80 mesh screen was weighed and recorded.

4. Analytical Assays a. HPLC Assay

This technique was utilized to quantitate the concentrations of Clarithromycin after both granulation steps were completed. The assay technique used is a standardized literature method.

b. Infrared (IR) Technique

This method of analysis was used to examine and compare the structural changes that might result when water is substituted for alcohol as the granulating solvent. The IR patterns of granules at various stages of granulation were compared with that of each component and granules obtained via alcohol granulation. Qualitative examination of each sample was conducted using an infrared spectrophotometer with potassium bromide pellets.

c. X-ray Powder Diffraction Measurement

Qualitative x-ray powder diffraction measurements of various samples were conducted using a Nicolet x-ray diffractometer (Micro-Vax computer system, Model I2 with software version 2.41. Siemens Analytical X-ray Distributors) measuring 25 points at each 2θ scattering angle and operating at room temperature.

d. Ether Extractable Analysis

This assay was primarily utilized to assess the concentration of free Clarithromycin after each granulation step. The ether extractable analysis has been developed based on the simple principle that CARBOPOL 947P and PVP are completely insoluble in ether, while Clarithromycin molecules have a very high ether solubility. As a result of interaction between Clarithromycin and CARBOPOL 947P molecules during the granulation process, the Clarithromycin-CARBOPOL 947P particles will remain insoluble in ether. Filtration of a mixture of these granules in ether leads to entrapment of any Clarithromycin-CARBOPOL 947P or Clarithromycin-CARBOPOL 947P-PVP particles, while the free Clarithromycin remains in the solution and is recovered when the solvent part of the filtered solution is evaporated. The detailed procedure may be found under Standard Control Procedure (SCP), list no. 31043, issued at Apr. 7, 1992 (Abbott Labs).

sured by ether extractable analysis) for a given granulation time. However, granulation at lower temperatures tended to result in the formation of a more fluid material, (since gel formation was more effectively retarded). At the higher concentrations of water (i.e., 2.0 kg of water/1.0 kg of powder), increasing the jacket temperature improved both the quality of particles formed (i.e., with respect to ease of fluidization) and decreased the concentration of ether extractables measured.

TABLE 2

| Exp. No. | Jacket Temp. (° C.) | Water Added (Kg) | Granulation Time (Minutes) | Appearance/ Drying Method | % LOD | % Ether Extractable Material |
|---|---|---|---|---|---|---|
| 1 | 0 | 1.61 | 60 | Easily fluidized | 1.0 | 14.0 |
| 2 | 0 | 1.61 | 120 | Basily fluidized | 1.2 | 9.0 |
| 3 | 0 | 2.0 | 60 | Paste/Tray dried | — | — |
| 4 | 0 | 2.5 | 60 | Paste/Tray dried | — | — |
| 5 | 12 | 1.61 | 60 | Easily fluidized | 2.1 | 15.0 |
| 6 | 12 | 1.61 | 120 | Easily fluidized | 1.0 | 7.0 |
| 7 | 12 | 2.0 | 60 | Overwet/fluidized | 0.9 | 8.0 |
| 8 | 12 | 2.5 | 60 | Overwet/fluidized | 1.1 | 1.6 |
| 9 | 12 | 2.5 | 120 | Paste/Tray dried | — | — |
| 10 | 0 | 2.0 | 60 + 60 | Easily fluidized | 0.9 | 2.5 |
| 11 | 12 | 1.6 | 60 + 30 | Easily fluidized | 3.3 | 3.7 |
| 12 | 12 | 1.6 | 60 + 60 | Easily fluidized | 2.8 | 1.8 |
| 13 | 12 | 1.61 | 60 + 60 | Easily fluidized | 0.9 | 1.1 |
| 14 | 12 | 1.8 | 60 + 30 | Easily fluidized | 4.5 | 6.1 |
| 15 | 12 | 1.8 | 60 + 60 | Basily fluidized | 2.6 | 5.7 |
| 16 | 12 | 2.0 | 60 + 60 | Overwet/fluidized | 1.0 | 1.3 |

e. Loss on Drying

Two gravimetric techniques, a vacuum oven at 60° C. and a Computrac at 110° C. were utilized to verify the concentration of water at different granulation stages.

f. Dissolution

The rate of dissolution for uncoated clarithromycin particles produced with aqueous granulation was compared with current (i.e., alcohol granulated) uncoated particles. The HPLC procedure utilized to assay is described above.

EXAMPLE 1

Formation of Clarithromycin/Carbopol 974P Granules in a 10 Liter GRAL

A. First Granulation

Preliminary experiments were designed to examine the different variables that may affect the first granulation process (of clarithromycin and carbomer). A multiple level factorial design was utilized to examine the aqueous granulation process. In these series of experiments, 625 grams of clarithromycin and 375 grams of CARBOPOL 974P (5:3 w/w) were used exclusively. The granulating solvent was 100% water. The effect of jacket temperature, rate of water addition and the total quantity of water added were the variables examined in this study. The effect of these variables on granulation was measured by determining (1) ease of fluidization and (2) % ether extractable material (i.e., Clarithromycin). Table 2 shows a summary of all experiments conducted in the 10 liter GRAL.

1. Effect of Jacket Temperature

As indicated in Table 2, at lower quantities of water (i.e., 1.6 kg of water/1.0 kg of powder), jacket temperature did not significantly effect the ease of fluidization of the granules and a 12° C. change in the jacket temperature did not affect the quality of final product (i.e., the extent of interaction between Clarithromycin and CARBOPOL 974P as mea- 2. Quantity of Water As also shown in Table 2, increasing the amount of water added at a given temperature for the same granulation time leads to formation of a paste, but improves (i.e., lowers) the ether extractable value. For example, at a jacket temperature of 12° C., increasing the concentration of water resulted in reduction of the ether extractable values from 15% (for 1.6 kg of water, see Exp. No. 5) to less than 10% (for 2.5 kg of water, see Exp. No. 8). Thus, it appears that increasing the amount of water improved the efficiency of interaction between Clarithromycin and CARBOPOL 974P molecules. The more effective interaction between polymer and drug may be attributed to the role of water in enhancing the flexibility of the polymer (as the glass transition temperature is reduced) and also increasing the concentration of Clarithromycin in solution phase. However, increasing water concentration leads to more extensive gelation which has the disadvantage of reducing the tendency for fluidization.

3. Granulation Time

Increasing the granulation time lead to lower ether extractable values for the same jacket temperature and water content as shown in Table 2 above. However, if the water was added over the first hour of granulation and then the material permitted to granulate for an additional period of time, the ether extractable values were further improved. For example, ether extractable values were reduced to less than 2% when water was added over the first hour and the material then granulated for an additional hour (see Exp. Nos. 12 and 13) as compared to a 7.0% ether extractable value when the water was continuously added over a 2 hour period (see Exp. No 6). Addition of water over the first hour of granulation allowed the total concentration of water to become available during the latter phase (i.e., second hour) for the interaction between Clarithromycin and CARBOPOL 974P molecules.

B. Second Granulation

The second granulation of particles was conducted with the jacket temperature set at 15° C. A 13.9% solution of PVP in distilled water or alcohol was used as the granulating solvent and the material was granulated for one hour. Table 3 shows the ether extractable results of five granulations, where an aqueous PVP solution at 13.9% concentration was used as the granulating solvent. As shown in this Table, the uncoated clarithromycin particles exhibit lower ether extractable values compared to granules formed after the first granulation step. For example, ether extractable values of 6.1% and 5.7% obtained after the first granulation were reduced to 2.6% and 1.8% respectively, after PVP granulation. Independent studies have shown that the granulation with PVP solution results in deposition of PVP on the outer surface of granules, hence a certain amount of drug masking by PVP in good agreement with lower ether extractable results (CMR Report No. 93276).

The aqueous clarithromycin and CARBOPOL 974P and aqueous PVP granulations were successfully scaled to the 75, 600 and 1200 liter GRAL high-sheer granulators. The uncoated particles showed similar physical and chemical characteristics to the current uncoated particles produced with the alcohol granulation. The aqueous granulation process showed the added advantage's of ease of handling and transfer. Evaluation of two types of mills, Comil and Fluid Air Mill, showed that the Comil with its shear milling action was not effective in reducing the size of uncoated particles produced via aqueous granulation.

EXAMPLE 2

Formation of Clarithromycin/Carbopol 974P Granules in a 600 Liter GRAL

A. First Granulation

To a 600 L GRAL mixing apparatus was added 6-O-methylerythromycin A (50 kg) and CARBOPOL 974P (B. F. Goodrich Co.) (30 kg). The GRAL jacket inlet temperature was set at 20° C. and the outlet temperature was set at 25° C. The mixer was set to low and granulator was set to low and the mixture was blended for 15 minutes. The mixer and granulator were set to low and distilled water (128.4 kg) was added through the GRAL's liquid addition port over 60 minutes. The GRAL was opened, the sides were scraped, and granulation was then continued for another 60 minutes.

The GRAL discharge chute was opened and the contents were quickly discharged into a dryer bowl. The dryer bowl was positioned in an Aeromatic fluid bed dryer and the granulation was dried (inlet air temperature 90° C., air flow 4500 CFM), until an outlet air temperature of 70° C. was reached, after which drying was continued for an additional 15 minutes, followed by a 15 minute cooling cycle. The granulation was then milled through a 0.625 inch hole band using a fluid air mill (reverse speed 2500 rpm, feed screw at 30 rpm), and redryed as described above. The dried granules were then milled through a 0.028 inch size band (forward speed at 3000 rpm, feed rate 30 rpm) in the fluid air mill.

B. Second Granulation

The milled granules were placed in a 600 L GRAL mixing apparatus, the GRAL jacket inlet temperature was set at 20° C. and the outlet temperature was set at 25° C. The mixer and granulator were set to low and a 15% solution of PVP K-90 in distilled water (46 kg) was added through the GRAL's liquid addition port over 60 minutes.

The dried granulation was then sifted over 30, 40, and 80 mesh screens using a Sweco sifter. The 40–80 mesh granules, and the smaller than 80 mesh granules were collected, and the greater than 30–40 mesh granules were milled in the fluid air mill (0.156 inch band, 2700 rpm, screw feeder at 30 rpm) to reduce oversized material. The milled granules were then sifted as described above and the 40–80 mesh granules were combined with those obtained above.

The above process was then repeated on four more 50 kg lots of 6-O-methylerythromycin A. The 40–80 mesh granules from all five runs were combined to give 291.9 kg of 40–80 mesh granules and 111.9 kg of fines (smaller than 80 mesh granules).

C. Regranulation of Fines

The fines (granules smaller than 80 mesh) from step B, were placed in a 600 L GRAL mixing apparatus, the GRAL jacket inlet temperature was set at 20° C. and the outlet temperature was set at 25° C. The mixer and granulator were set to low and distilled water (60 kg) was added through the GRAL's liquid addition port over 60 minutes. The regranulated material was then discharged from the GRAL and dried in the fluid bed drier as described in Example 1, step B above. The dried, regranulated material was then sifted over 30, 40, and 80 mesh screens using a Sweco sifter to give 70.9 kg of 40–80 mesh granules and 38.9 kg of less than 80 mesh particles. The total yield of 40–80 mesh 6-O-methylerythromycin granules from both Examples 1 and 2 was 362.8 kg which represents a yield of 83% of theoretical.

EXAMPLE 3

Formation of Clarithromycin/Carbopol 974P Granules in a 600 Liter GRAL

A. First Granulation

The granulation parameters in the 600 liter GRAL were also studied with production batch sizes of 66.7 and 80 kg. The quantity of each ingredient was linearly increased according to the batch size utilized. FIG. 1 shows the head space temperature as a function of granulation time for different clarithromycin and CARBOPOL 947P granulation runs, using a 66.7 kg batch size. Based on the results from 10 and 75 liter GRAL studies, initially an inlet/outlet jacket temperature of 12°/14° C. was utilized. However, comparison of the head space temperatures for the first granulation showed somewhat lower values compared to the similar granulation runs conducted in the 75 liter GRAL (data not shown). More efficient mixing of granules in the 600 liter GRAL and the smaller relative batch size may be responsible for the observed low head space temperatures. Furthermore, the cooling system utilized to control the jacket temperature in the 600 liter GRAL operates on a negative feedback mechanism, so that any heat generated during the process that might lead to an increased outlet temperature is offset by an automatic lowering of inlet temperature. Based on earlier studies, it was shown that the head space temperatures indirectly provide some information regarding the extent of interaction between the clarithromycin and CARBOPOL 947P molecules, thus some adjustment of jacket temperature was deemed necessary to obtain the desired head space temperatures. Increasing the inlet/outlet jacket temperature to 20°/25° C. provided the necessary temperature, where the head space temperatures of above 30° C., required for the effective interaction between clarithromycin and CARBOPOL 947P molecules, were achieved. Table 9 shows the results of ether extractable and LOD tests for various clarithromycin and CARBOPOL 947P granulations. From these results, increasing the jacket temperature to 20°/25° C. leads to reduction of ether extractable values, in good agreement with the observed increase in the head space temperatures (FIG. 1). Comparison of head space temperatures between the 75 and 600 liter GRALs showed a much smaller concentration of heat accumulation in the 600 liter GRAL with a 66.7 kg batch, where the temperature increase during the latter stage of granulation was limited to only a few degrees.

Figure 2:
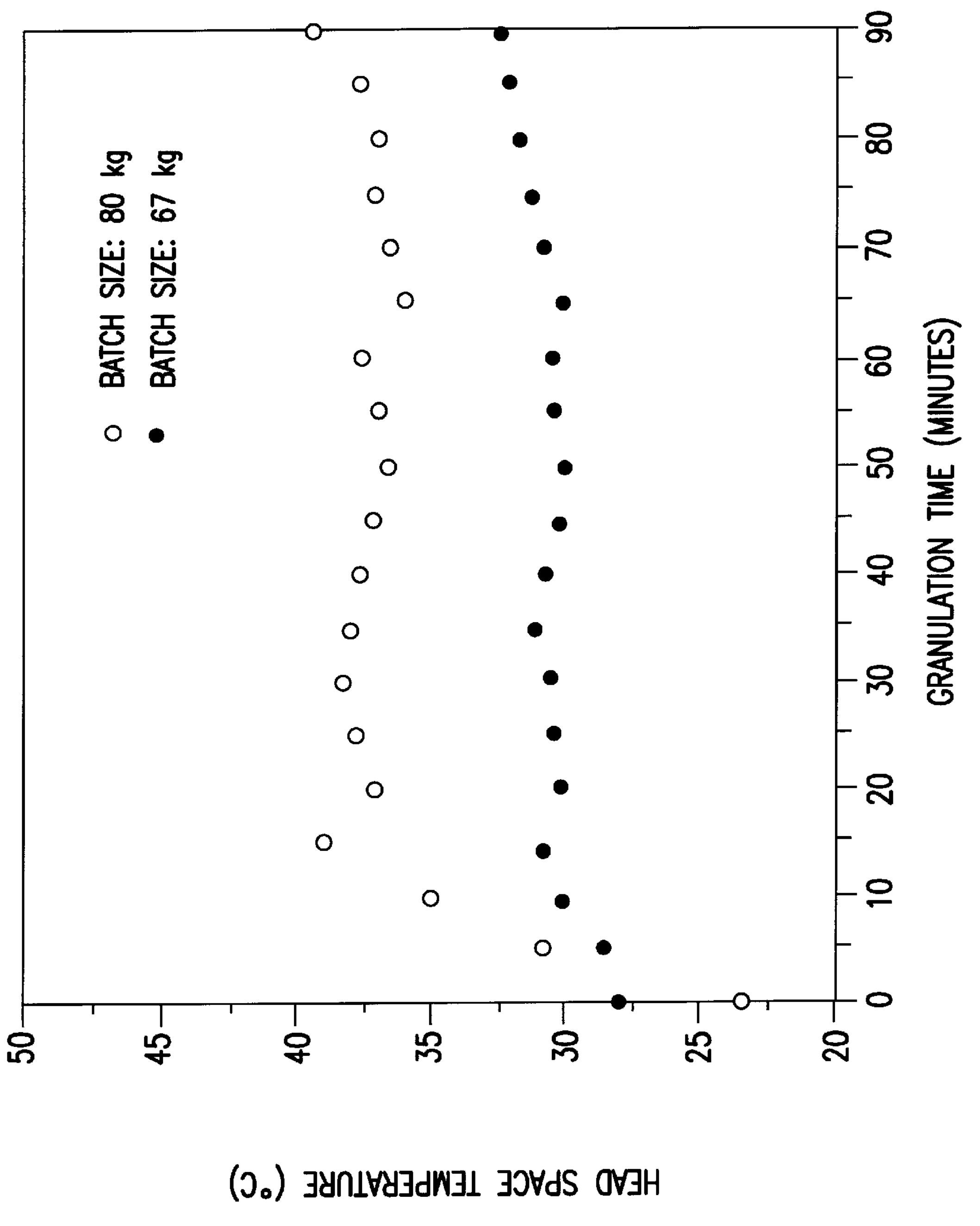
FIG. 2 shows a graph of head space temperature as a function of granulation time and batch size for clarithromycin-CARBOPOL 974P granulations in a 600 liter GRAL.

FIG. 2 shows the comparison of head space temperatures for two different granulation runs with 66.7 and 80 kg batch size (at 20°/25° C. jacket temperature), respectively. As expected, the larger batch size led to higher measured head space temperatures. Lower ether extractable values (shown in Table 3 below) obtained with 80 kg batch size are in good agreement with the higher head space temperatures observed.

TABLE 3

| Lot No. | Batch Size (Kg) | Granulation Time (mins.) | % LOD | % Ether Extractable Material |
|---|---|---|---|---|
| R2 | 66.67 | 60 + 30 | 2.3 | 7.5, 7.6 |
| R3 | 66.67 | 60 + 60 | 5.0 | 4.6, 4.6 |
| R4 | 80.0 | 60 + 30 | 1.4 | 4.4 |
| R5 | 80.0 | 60 + 60 | 1.2 | 1.8 |

B. Second Granulation

The second granulation of clarithromycin particles was conducted over one hour at different jacket temperatures as shown in Table 4 below. Increasing the jacket temperature had no significant effect on the PVP granulation step.

TABLE 4

| Second Granulation Lot No. | Set Jacket Temperature Inlet/Outlet (°C.) | First Granulation Lot No. | % LOD | % Ether Extractable Material |
|---|---|---|---|---|
| R1 | 12/14 | R1 | 1.2 | 2.5 |
| R2 | 15/18 | R2 | 0.8 | 1.4 |
| R3 | 15/20 | R3 | 0.7 | 0.9 |
| R4 | 20/25 | R4 | 0.6 | 1.2 |

C. Second Granulation with Incorporation of Fines

Figure 3:
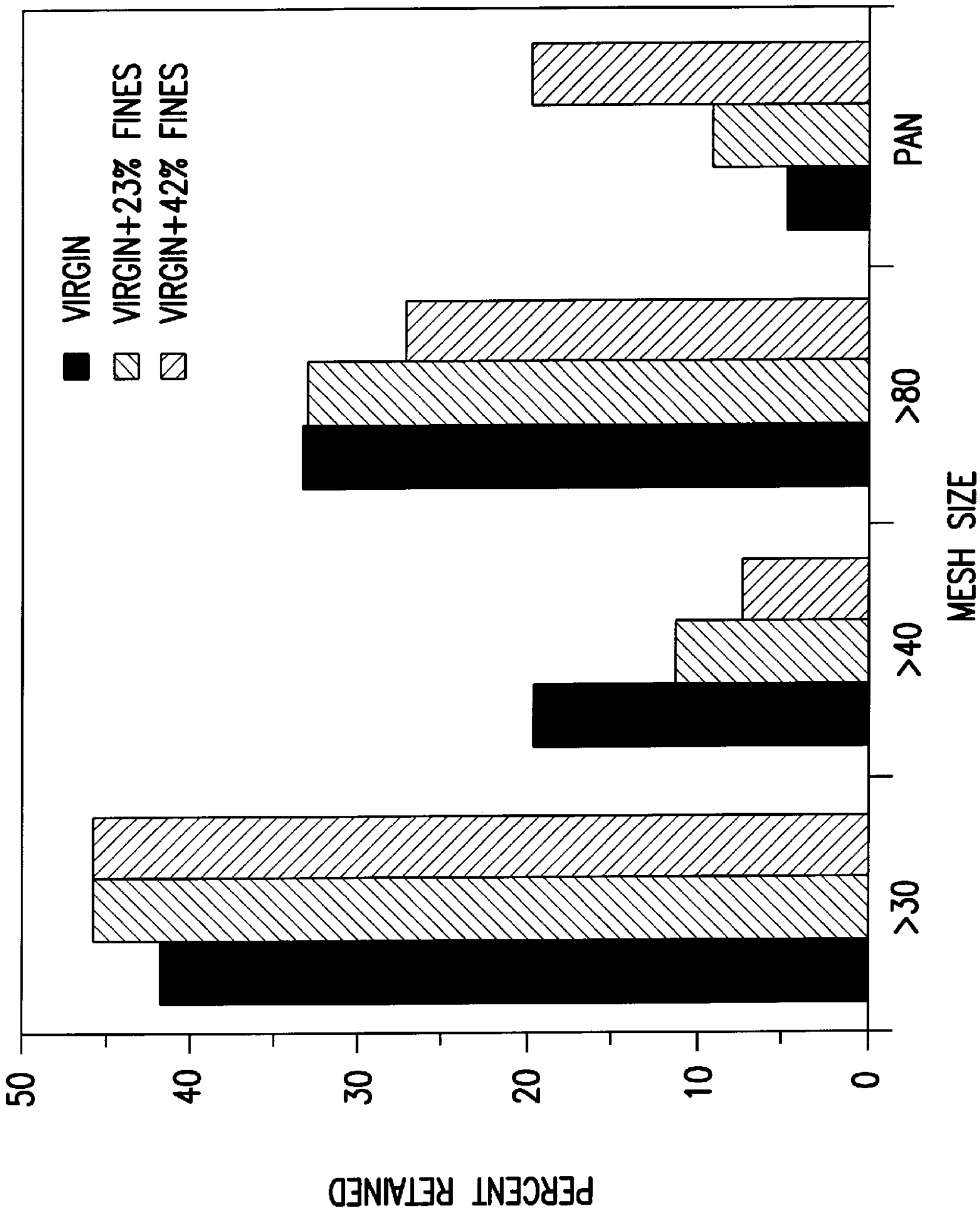
FIG. 3 is a graph showing a comparison of particle size distribution for uncoated clarithromycin particles produced in a 600 liter GRAL and the effect of incorporation of fines during PVP granulation.

To minimize the processing time:, evaluation of the effect of incorporation of the fines into the second PVP granulation as a means of eliminating the regranulation step was attempted. Experiments were conducted where two different concentrations of fines were incorporated into the PVP granulation step. FIG. 3 compares the particle size distribution for these granulation trial with the virgin uncoated clarithromycin particles after the granules were sized using a Sweco system. As shown in this graph, no significant improvement in the concentration of uncoated particles retained over the 80 mesh screen (i.e., yield) was observed. However, increasing the concentration of fines incorporated into the aqueous granulation was shown to result in an increase of the percent fines generated in an almost linear relationship to the concentration of fines initially incorporated. This result suggests that incorporating the fines into the second granulation will reduce the yield of 40–80 mesh particles generated.

Figure 4:
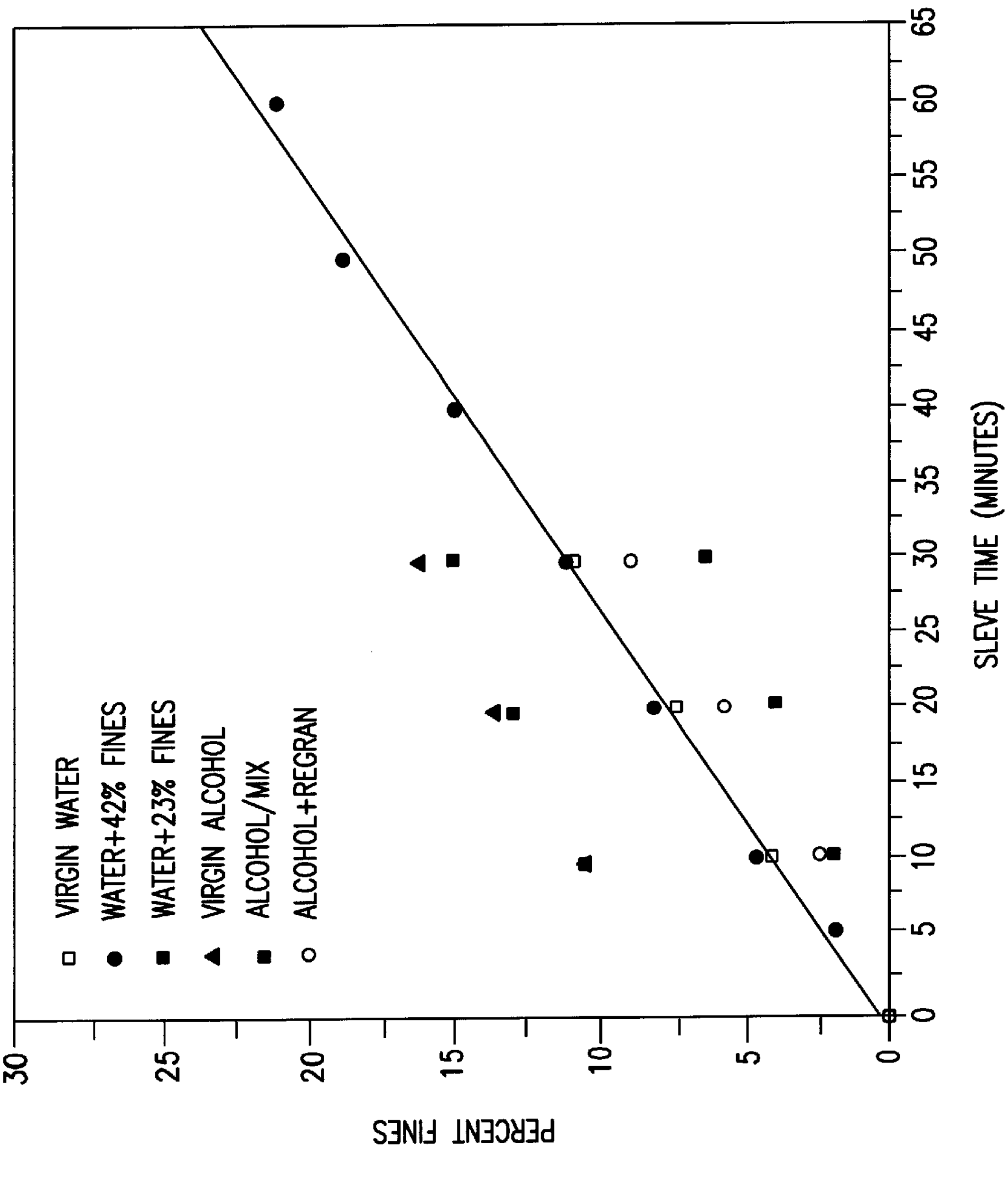
FIG. 4 is a graph showing a comparison of percent fines generated as a function of sieving time for uncoated clarithromycin particles produced in the 600 liter GRAL and the effect of incorporation of fines during PVP granulation.

FIG. 4 shows the result of granule hardness testing for various aqueous and alcohol granulations. Comparison of the percent fines generated for different granulations shows relatively hard particles when uncoated particles were produced via an aqueous granulation (regardless of the presence or absence of fines incorporated) compared to similar uncoated particles granulated using alcohol. Comparison of two different alcohol granulation, virgin material (following PVP granulation) and a blend of virgin granules with regranulated particles of 40–80 mesh size did not show a significant change. Thus, it appears that once the 40–80 mesh particles are formed, they do not vary significantly in hardness or strength.

D. Regranulation

Regranulation of fines was carried out using distilled water and 3% PVP solution at a rate of 1 kg/minute with the inlet/outlet jacket temperature of 20°/25° C. Comparison of regranulation runs using two different granulating solutions resulted in a similar concentration of 40–80 mesh particles, suggesting no significant improvement of yield due to the presence of PVP. The percent 40–80 mesh particles after both regranulation runs was calculated to be about 55%.

EXAMPLE 4

Formation of Clarithromycin/Carbopol 974P Granules in a 1200 Liter GRAL

Figure 5:
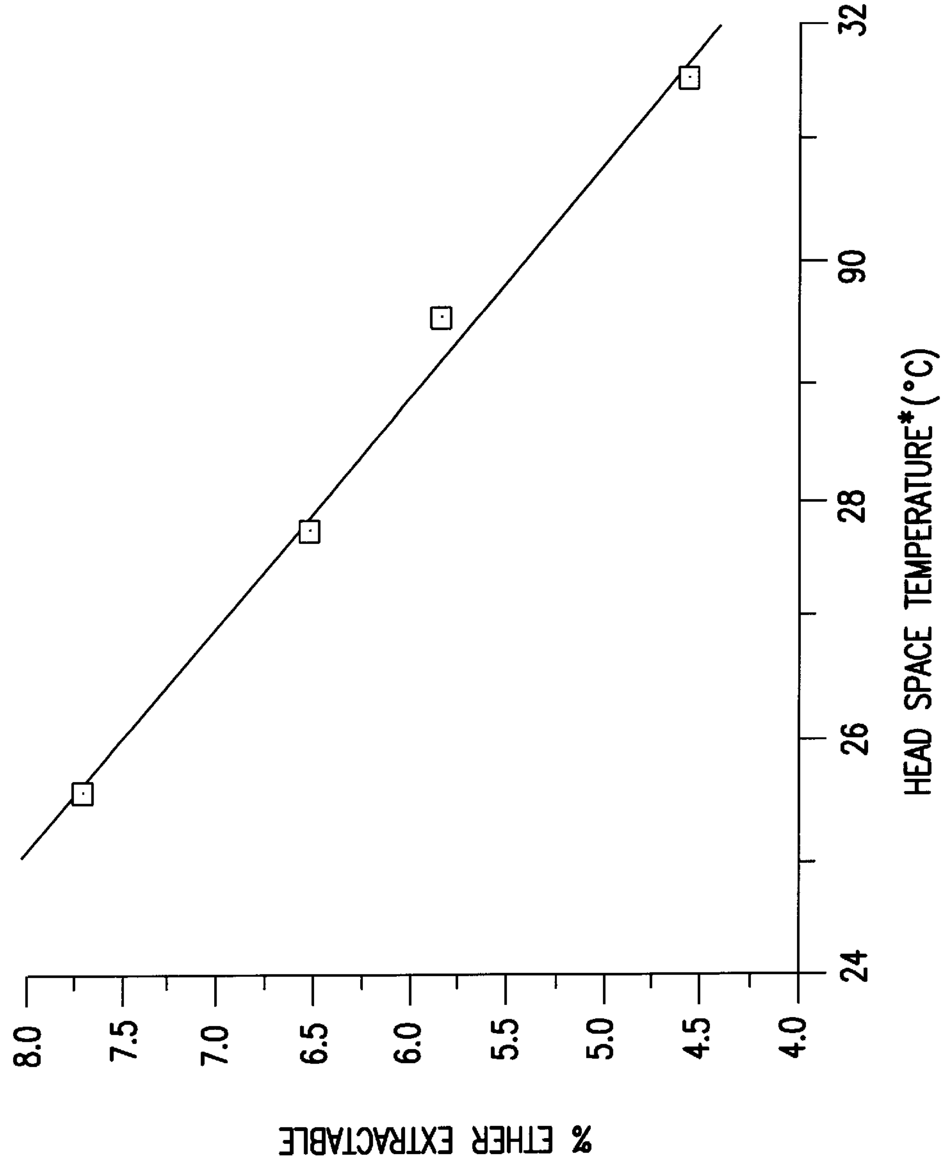
FIG. 5 shows a graph of ether extractable material as a function of head space temperature for clarithromycin-CARBOPOL 974P granulations in a 600 liter GRAL. The asterisk (*) indicates that the head space temperatures were obtained at the end of the first granulation for a batch size of 67 kg.
Figure 6:
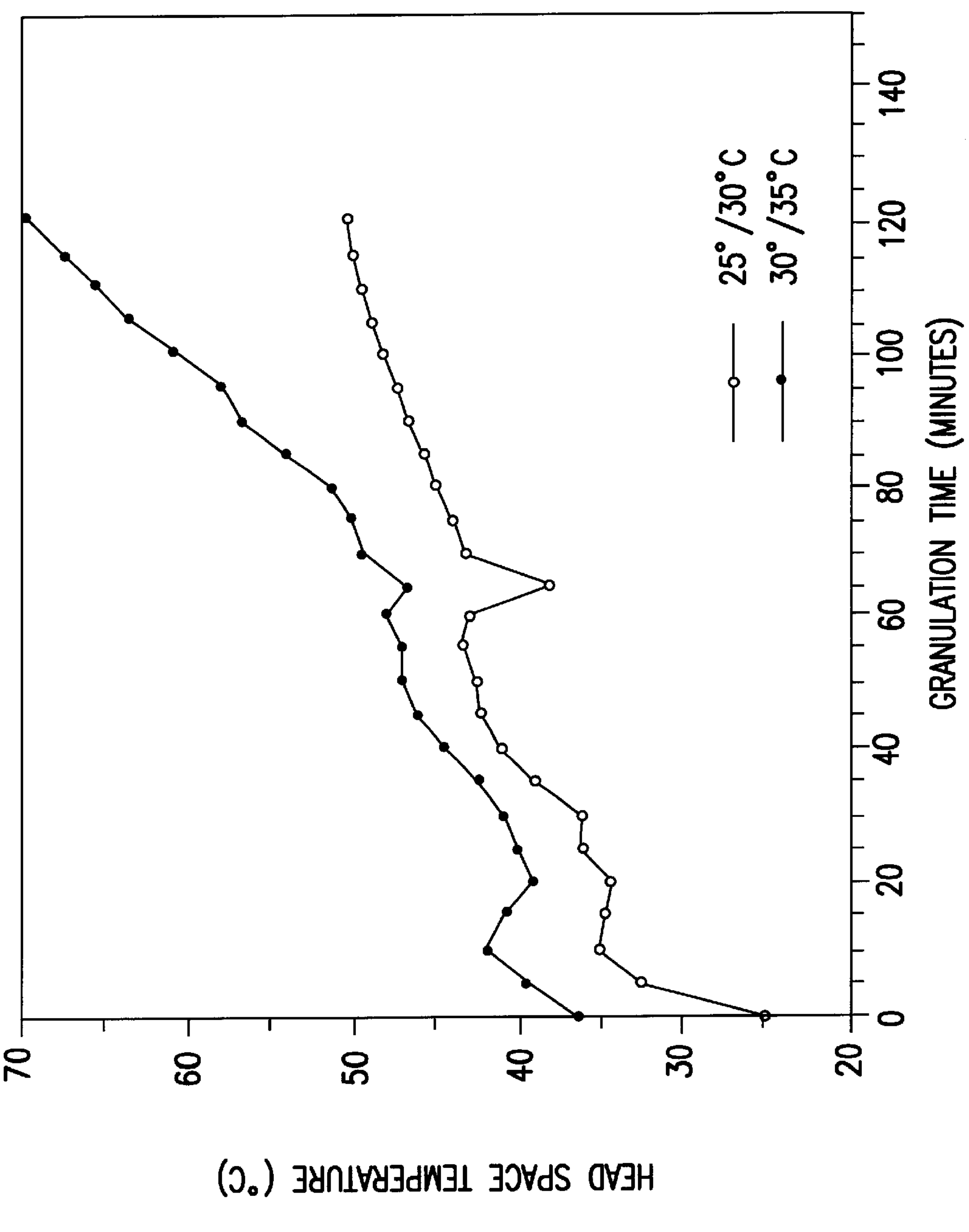
FIG. 6 shows a graph of head space temperature as a function of granulation time for clarithromycin-CARBOPOL 974P granulations in a 1200 liter GRAL having a jacket temperature of 25° C./30° C. and 30° C./35° C.
Figure 7:
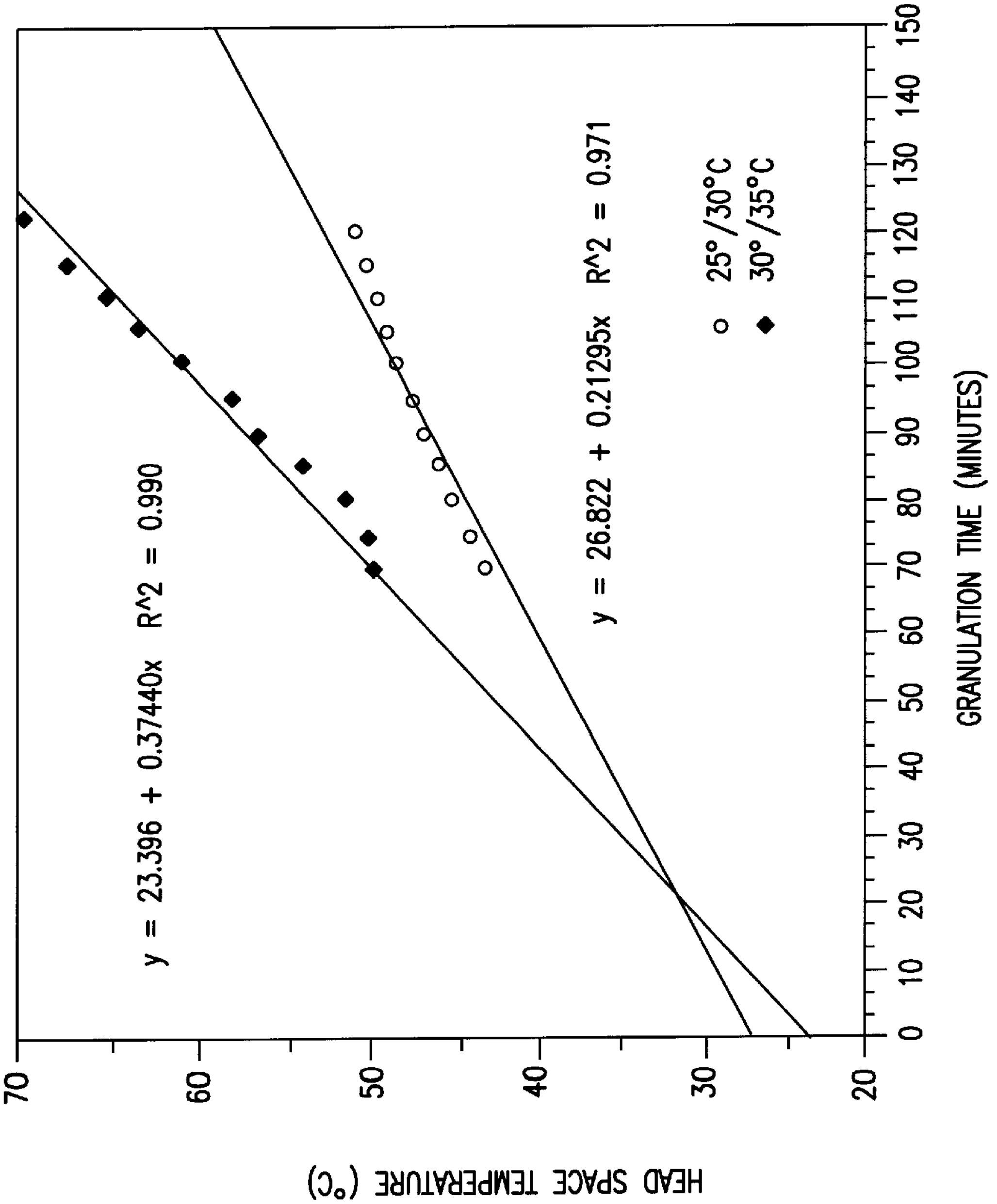
FIG. 7 is a graph showing the linear relationship of the values presented in FIG. 6.

A single experimental granulation run in a 1200 liter GRAL with inlet/outlet jacket temperatures of 20° C./25° C. was conducted essentially as in Example 3. The material processed adequately, however, the reported either extractable value after the second granulation run (i.e., PVP granulation) was above the process control of 1.0% (i.e., 1.6%). Based on the previous studies in the 600 GRAL, a direct relationship between the ether extractable values and the head space temperatures measured during the granulation run was shown, where higher head space temperatures during the first granulation generally lead to a lower ether extractable result (FIG. 5). Based on these findings and in order to improve the ether extractable values for the granulations conducted in the 1200 GRAL, two additional experimental runs using higher preset jacket temperatures of 25° C./30° C. and 30° C./35° C. were carried out. FIG. 6 shows the head space temperatures as a function of time for both first granulation runs conducted in the 1200 liter GRAL. As shown in this Figure, the head space temperatures increase slightly during the water addition step followed by a rapid increase after all the water has been added (i.e., during the second hour of granulation). Least square fit of the head space temperature data during the second hour of first granulation shows a linear relationship with the granulation time, where a higher slope for the experiment conducted at the higher jacket temperature was calculated (FIG. 7). However, comparison of measured either extractable values after the first granulation did not show a significant difference, once the jacket temperature was increased above 20° C./25° C. Alternatively, the measured ether extractables after the PVP granulations showed slightly lower values for the granulation run with the higher jacket temperature settings. Thus it appears that while the reduction of ether extractable values during the PVP granulation in the 600 liter GRAL is not significantly affected by the jacket temperatures, increasing the temperature of the jacket during this latter granulation step may lead to somewhat lower either extractable values in the 1200 liter GRAL. Two additional granulations at the 1200 liter GRAL were conducted to evaluate the effect of higher jacket temperature settings (shown in Table 5).

TABLE 5

| Granulation | Jacket Temperature Inlet/Outlet (°C.) | % Ether Extractable Material |
|---|---|---|
| First Granulation | | |
| Run 1 | 25/30 | 1.1 |
| Run 2 | 30/35 | 1.1 |

TABLE 5-continued

| Granulation | Jacket Temperature Inlet/Outlet (°C.) | % Ether Extractable Material |
|---|---|---|
| Second Granulation | | |
| Run 3 | 25/30 | 0.9 |
| Run 4 | 30/35 | 0.4 |

Figure 8:
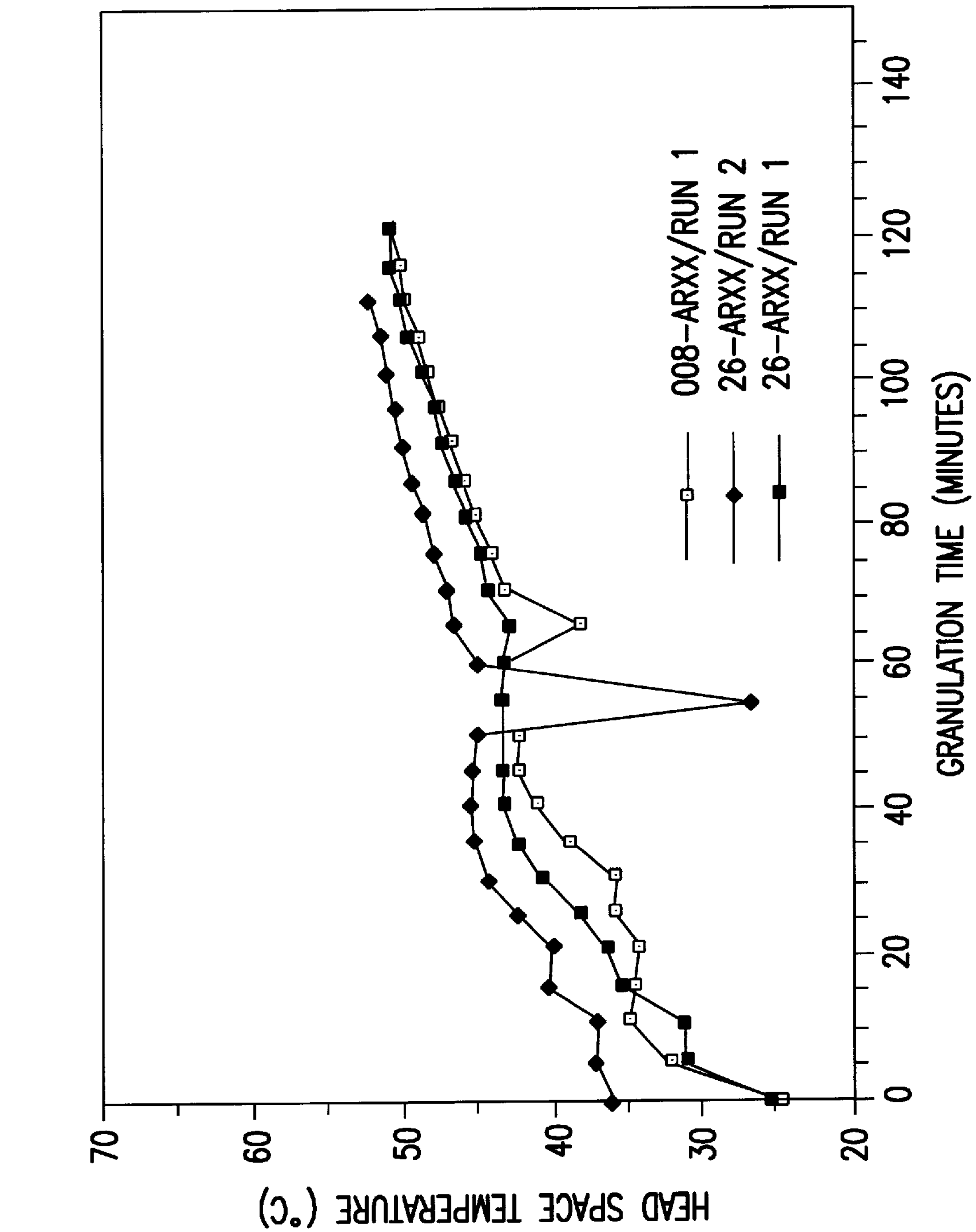
FIG. 8 shows a graph of head space temperature as a function of granulation time for clarithromycin- CARBOPOL 974P granulations in a 1200 liter GRAL having a jacket temperature of 25° C./30° C.

FIG. 8 shows good reproducibility for the head space temperatures as a function of granulation time for three different "first" granulation runs performed at the same jacket temperature of 25° C./30° C. The ether extractable values obtained after the first and second granulations are shown in Table 6 below, where these values meet the required limit after the second granulation (no specific either extractable limit is required after first granulation). Based on this result, it is thus desirable to modify the inlet/outlet jacket temperature settings for the 1200 liter GRAL granulations to 25° C./30° C. for the first granulation step and 30° C./35° C. for the second granulation step.

TABLE 6

| Granulation | Jacket Temperature Inlet/Outlet (°C.) | % Ether Extractable Material |
|---|---|---|
| First Granulation | | |
| Run 1 | 25/30 | 2.9, 5.2, 3.7 (3.9)* |
| Run 2 | 25/30 | 5.1, 4.8, 3.7 (4.5)* |
| Second Granulation | | |
| Run 3 | 30/35 | 0.3, 0.6, (0.4)* |
| Run 4 | 30/35 | 0.2, 0.4, 0.4 (0.3)* |

What is claimed is:

1. A process for preparing granules of a macrolide antibiotic, comprising the steps of:

(a) mixing a macrolide antibiotic and a carbomer in a weight ratio of between about 1:10 and about 5:2;

(b) wetting the mixture with an aqueous solvent;

(c) blending the mixture for a time sufficient to allow formation of macrolide antibiotic-carbomer granules, said blending being accomplished in a vessel having a head space which is maintained at a temperature from about 0 to about 70° C.; and (d) drying the macrolide antibiotic-carbomer granules.

2. A process according to claim 1 wherein the carbomer is an acrylic polymer.

3. A process according to claim 2 wherein the carbomer is CARBOPOL 974P acrylic acid polymer.

4. A process according to claim 1 wherein the antibiotic macrolide is selected from the group consisting of an erythromycin and a clarithromycin.

5. A process according to claim 4 wherein the antibiotic macrolide is clarithromycin.

6. A process according to claim 2 wherein the mixture formed in step (a) comprises clarithromycin and acrylic polymer in a ratio of between about 1:10 and about 5:2.

7. A process according to claim 6 wherein the mixture is wetted in step (b) with between about 1.5 and about 2.5 parts water by weight.

8. A process according to claim 1 wherein the mixture is wetted in step (b) with between about 1.5 and about 2.5 parts water by weight.

9. A process according to claim 1 wherein the granules consist of predominantly 40–80 mesh particles.

10. A process according to claim 1 further comprising the additional step, prior to step (d), of mixing the macrolide antibiotic-carbomer granules formed in step (c) with an aqueous solution of a binder.

11. A process according to claim 10 wherein the binder is polyvinylpyrrolidone.

12. A process according to claim 1 wherein the head space temperature is maintained by means of a water jacket.

13. A process according to claim 12 wherein the head space temperature is maintained at a temperature from about 30 to about 50° C.

14. A process according to claim 13 wherein the head space temperature is maintained by maintaining the water jacket inlet temperature at about 20 to about 40° C.

15. A process for the preparation of pharmaceutical granules comprising clarithromycin and CARBOPOL 974P acrylic acid polymer comprising the steps of:

(a) mixing the clarithromycin and polymer in a ratio of between about 5:2 and about 5:3 by weight;

(b) wetting the mixture with between about 1.5 and about 2.5 parts water by weight;

(c) blending the mixture for a time sufficient to allow formation of clarithromycin-CARBOPOL 974P granules, said blending being accomplished in a vessel having a headspace which is maintained at a temperature from about 30 to about 50° C.;

(d) regranulating the clarithromycin-CARBOPOL 974P granules using an aqueous solution of polyvinylpyrrolidone; and (e) drying the clarithromycin-CARBOPOL 974P granules.

16. A process according to claim 1 wherein the aqueous solvent of step (b) is essentially free of organic solvents.

17. A pharmaceutical formulation comprising clarithromycin-CARBOPOL 974P granules prepared according to the process of claim 15.

18. A process according to claim 10 wherein the granules consist of predominantly 40–80 mesh particles.

* * * * *